United States Patent
Bhushan et al.

(10) Patent No.: US 11,219,594 B2
(45) Date of Patent: *Jan. 11, 2022

(54) EFFERVESCENT COMPOSITIONS OF METFORMIN AND PROCESSES FOR PREPARATION THEREOF

(71) Applicant: STEERLIFE INDIA PRIVATE LIMITED, Bengaluru (IN)

(72) Inventors: Indu Bhushan, Bengaluru (IN); Vijay Kulkarni, Bengaluru (IN); Rakshith Shetty, Bengaluru (IN)

(73) Assignee: STEERLIFE INDIA PRIVATE LIMITED, Bengaluru (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/781,090

(22) PCT Filed: Dec. 12, 2016

(86) PCT No.: PCT/IB2016/057530
§ 371 (c)(1),
(2) Date: Jun. 1, 2018

(87) PCT Pub. No.: WO2017/098481
PCT Pub. Date: Jun. 15, 2017

(65) Prior Publication Data
US 2018/0360737 A1 Dec. 20, 2018

(30) Foreign Application Priority Data
Dec. 12, 2015 (IN) .......................... 6681/CHE/2015

(51) Int. Cl.
*A61K 45/06* (2006.01)
*A61K 9/00* (2006.01)
*A61K 9/48* (2006.01)
*A61K 9/20* (2006.01)
*A61K 9/46* (2006.01)
*A61P 3/10* (2006.01)
*A61K 31/155* (2006.01)

(52) U.S. Cl.
CPC .......... *A61K 9/0007* (2013.01); *A61K 31/155* (2013.01); *A61P 3/10* (2018.01)

(58) Field of Classification Search
CPC .. A61K 9/0056; A61K 9/2077; A61K 9/0007; A61K 9/2095; A61K 2300/00; A61K 9/006; A61K 9/0053; A61K 9/0095; A61K 45/06; A61K 9/48; A61K 2800/92; A61K 9/20; A61P 3/10; A61L 2300/602; A61L 15/44
See application file for complete search history.

(56) References Cited

U.S. PATENT DOCUMENTS

| 1,450,865 | A |   | 4/1923 | Pelc |
|---|---|---|---|---|
| 2,071,841 | A |   | 2/1937 | Kelling |
| 2,851,361 | A |   | 9/1958 | Diller |
| 2,988,562 | A |   | 6/1961 | Weinmayr |
| 3,663,271 | A |   | 5/1972 | Gergely |
| 3,773,922 | A |   | 11/1973 | Gergely et al. |
| 4,004,036 | A |   | 1/1977 | Schmitt |
| 4,252,664 | A |   | 2/1981 | Inamorato |
| 4,305,502 | A |   | 12/1981 | Gergely et al. |
| 4,371,516 | A |   | 2/1983 | Gregory et al. |
| 4,614,648 | A |   | 9/1986 | Bru |
| 4,678,661 | A | * | 7/1987 | Gergely ................... A23L 2/40 424/44 |
| 4,824,664 | A |   | 4/1989 | Tarral et al. |
| 5,019,302 | A |   | 5/1991 | Sparks et al. |
| 5,055,306 | A |   | 10/1991 | Barry et al. |
| 5,178,878 | A |   | 1/1993 | Wehling et al. |
| 5,188,825 | A |   | 2/1993 | Iles et al. |
| 5,223,246 | A |   | 6/1993 | Kondo et al. |
| 5,302,396 | A |   | 4/1994 | Phadke et al. |
| 5,529,789 | A |   | 6/1996 | Lo |
| 5,631,023 | A |   | 5/1997 | Kearney et al. |
| 5,667,807 | A | * | 9/1997 | Hurner ..................... A61J 3/06 424/489 |
| 5,738,875 | A |   | 4/1998 | Yarwood et al. |
| 5,750,061 | A |   | 5/1998 | Farina et al. |
| 5,792,473 | A |   | 8/1998 | Gergely et al. |
| 5,827,541 | A |   | 10/1998 | Yarwood et al. |
| 5,969,181 | A |   | 10/1999 | Joerg et al. |

(Continued)

FOREIGN PATENT DOCUMENTS

| CA | 2331671 | C | * | 1/2008 | ........... A61K 9/0007 |
|---|---|---|---|---|---|
| CN | 102860302 | | | 1/2013 | |

(Continued)

OTHER PUBLICATIONS

Int'l Search Report and Written Opinion for Int'l Appln. No. PCT/IB2016/057530, dated Mar. 23, 2017.
Amela et al., "Methods for the Determination of the Carbon Dioxide Evolved From Effervescent Systems," Drug Development and Industrial Pharmacy, 19(9), 1019-1036, 1993.
Aslani et al., "Formulation, Characterization and Physicochemical Evaluation of Potassium Citrate Effervescent Tablets," Advanced Pharmaceutical Bulletin, 2013, 3(1), 217-225.

(Continued)

*Primary Examiner* — Tracy Liu

(74) *Attorney, Agent, or Firm* — Workman Nydegger

(57) ABSTRACT

The present invention relates to effervescent compositions of Metformin and optionally other anti-diabetic agents and processes for preparation thereof. More particularly provides an effervescent composition comprising Metformin, an acid and a base such that the composition is free of affirmatively added binders and granulating solvents. The effervescent composition of the present invention has retained carbon dioxide content of at least 90% of the input blend.

6 Claims, No Drawings

(56) References Cited

U.S. PATENT DOCUMENTS

| | | | |
|---|---|---|---|
| 5,976,577 | A | 11/1999 | Green et al. |
| 6,024,981 | A | 2/2000 | Khankari et al. |
| 6,071,539 | A | 6/2000 | Robinson et al. |
| 6,190,697 | B1 | 2/2001 | Gergely et al. |
| 6,221,392 | B1 | 4/2001 | Khankari et al. |
| 6,269,615 | B1 | 8/2001 | Amborn et al. |
| 6,426,111 | B1 * | 7/2002 | Hirsch ............... A23L 2/40 426/118 |
| 6,440,926 | B1 | 8/2002 | Spadoni et al. |
| 6,488,961 | B1 | 12/2002 | Robinson et al. |
| 6,544,551 | B1 | 4/2003 | Engel et al. |
| 6,649,186 | B1 | 11/2003 | Robinson et al. |
| 6,683,043 | B1 | 1/2004 | Dovey et al. |
| 6,764,601 | B1 | 7/2004 | Levy et al. |
| 7,208,175 | B2 | 4/2007 | Schroeder et al. |
| 7,507,396 | B2 | 3/2009 | Aldritt et al. |
| 7,910,030 | B2 | 3/2011 | Jean-Paul et al. |
| 7,964,212 | B2 | 6/2011 | McCallister et al. |
| 7,972,623 | B2 | 7/2011 | Gergely et al. |
| 8,329,196 | B2 | 12/2012 | Jacobi et al. |
| 8,449,906 | B2 | 5/2013 | McCallister et al. |
| 8,545,879 | B2 | 10/2013 | Burns et al. |
| 8,545,881 | B2 | 10/2013 | Venkatesh et al. |
| 8,637,076 | B2 | 1/2014 | Habib et al. |
| 2001/0006677 | A1 | 7/2001 | McGinity et al. |
| 2001/0041165 | A1 | 11/2001 | Katdare et al. |
| 2003/0003147 | A1 | 1/2003 | Katdare et al. |
| 2003/0170301 | A1 | 9/2003 | Wehling |
| 2004/0137058 | A1 | 7/2004 | Katdare et al. |
| 2004/0265375 | A1 | 12/2004 | Platteeuw et al. |
| 2004/0265380 | A1 | 12/2004 | Delmas et al. |
| 2006/0008521 | A1 | 1/2006 | Yeli et al. |
| 2006/0034921 | A1 | 2/2006 | Katdare et al. |
| 2006/0134195 | A1 | 6/2006 | Fu et al. |
| 2006/0240103 | A1 | 10/2006 | McCallister et al. |
| 2008/0031825 | A1 | 2/2008 | Chen et al. |
| 2008/0187558 | A1 | 8/2008 | Jacobi et al. |
| 2010/0021393 | A1 | 1/2010 | Chen et al. |
| 2010/0034889 | A1 | 2/2010 | Rau et al. |
| 2010/0172981 | A1 | 7/2010 | Gruber et al. |
| 2011/0039293 | A1 | 2/2011 | Hernandez Sierra |
| 2011/0281008 | A1 | 11/2011 | Gootenilleke et al. |
| 2011/0287114 | A1 | 11/2011 | Johnson |
| 2012/0009129 | A1 | 1/2012 | Brzeczko |
| 2013/0028844 | A1 | 1/2013 | Bilgic |
| 2013/0217777 | A1 | 8/2013 | Kirkorian |
| 2013/0287706 | A1 | 10/2013 | Hayward et al. |
| 2014/0066413 | A1 | 3/2014 | Howard et al. |
| 2017/0252295 | A1 | 9/2017 | Padmanabhan et al. |

FOREIGN PATENT DOCUMENTS

| | | | |
|---|---|---|---|
| CN | 102823622 | | 12/2013 |
| CN | 102823589 | | 6/2014 |
| DE | 102012102414 | A1 | 10/2013 |
| EP | 203768 | | 5/1993 |
| EP | 0975723 | A1 | 2/2000 |
| EP | 1077684 | A1 | 2/2001 |
| EP | 711560 | | 6/2001 |
| EP | 1274398 | A2 | 1/2003 |
| EP | 1301186 | A1 | 4/2003 |
| EP | 1404296 | | 4/2004 |
| EP | 2007347 | A2 | 12/2008 |
| EP | 2416756 | A2 | 2/2012 |
| EP | 2566451 | A1 | 3/2013 |
| EP | 2649989 | | 10/2013 |
| GB | 1338071 | | 11/1973 |
| GB | 2307857 | | 11/1999 |
| IN | 522/DEL/2010 | | 1/2012 |
| JP | 2004016148 | | 5/2006 |
| KR | 10-2014-0131205 | A | 11/2014 |
| WO | 1997/025030 | | 7/1997 |
| WO | 1998/003088 | | 1/1998 |
| WO | 1998/046715 | | 10/1998 |
| WO | 2000/034422 | | 6/2000 |
| WO | 2001/080822 | | 11/2001 |
| WO | 2002/098388 | | 12/2002 |
| WO | 2003/017986 | | 3/2003 |
| WO | 2002/005820 | | 4/2003 |
| WO | 1999/059553 | | 8/2003 |
| WO | WO-2006092711 A2 * | | 9/2006 ............ A61K 9/209 |
| WO | 2007/038979 A1 | | 4/2007 |
| WO | 2007/098924 | | 9/2007 |
| WO | WO-2009071954 A1 * | | 6/2009 ........... A61K 9/0007 |
| WO | 2010/117346 | | 2/2012 |
| WO | 2012/064306 | | 5/2012 |
| WO | 2011/139251 | | 3/2013 |
| WO | 2013/077822 A1 | | 5/2013 |
| WO | WO-2013077822 A1 * | | 5/2013 ........... A61K 9/0007 |

OTHER PUBLICATIONS

Carr, "Classifying Flow Properties of Solids," Chemical Engineering, 72(2), pp. 69-72, Feb. 1, 1965.

Carr, "Evaluating Flow Properties of Solids," Chemical Engineering, 72(1), pp. 163-168, Jan. 18, 1965.

Crowley et al., "Pharmaceutical Applications of Hot-Melt Extrusion: Part I," Drug Development and Industrial Pharmacy, 33:909-926, 2007.

Dejan Djuric, "Continuous Granulation with a Twin-Screw Extruder," Dissertation by Dejan Djuric, Germany, Jun. 2008, 112 pages.

European Pharmacopoeia 7.0, published 2010, pp. 714, 727 and 737.

Haack et al., TOPO Granulation Technology, TechnoPharm 2, Nr. 3, 186-191, 2012.

Hancock et al., "The Relative Densities of Pharmaceutical Powders, Blends, Dry Granulations and Immediate release tablets," Pharmaceutical Technology, Apr. 2003, pp. 64-78.

Hausner, "Friction Conditions in a Mass of Metal Powder," International Journal of Powder Metallurgy, 3(4): 7 pages, 1967.

Maniruzzaman et al., "A Review of Hot-Melt Extrusion: Process Technology to Pharmaceutical Products," International Scholarly Research Network ISRN Pharmaceutics vol. 2012, Article ID 436763, 9 pages, 2012.

McLaughlin et al., "Orally Disintegrable Tablets the Effect of Recent FDA Guidance on ODT Technology and Applications," Pharmaceutical Technology, Sep. 2009 issue, 8 pages.

Tousey, MD "The Granulation Process 101 Basic Technologies for Tablet Making," Pharmaceutical Technology Tableting and Granulation, 2002, pp. 9-13.

Podczeck, International Journal of Pharmaceutics, 142, 1996 (Year 1996).

Reddy et al., "Conventional and Patented Technologies in oral dispersible tablets: A Review," Journal of Chemical and Pharmaceutical Sciences, vol. 6, issue 4, pp. 286-292, 2013, 7 pages.

Repka, "Hot-Melt Extrusion," American Pharmaceutical Review, Russell Publishing, vol. 12, No. 6, Oct. 1, 2009, pp. 18-27, 10 pages.

International Search Report and Written Opinion received in PCT Application No. PCT/IB2015/000400, dated Aug. 31, 2015, 13 pages.

Non-Final Office Action received for U.S. Appl. No. 15/512,515, dated May 26, 2021, 23 pages.

\* cited by examiner

EFFERVESCENT COMPOSITIONS OF METFORMIN AND PROCESSES FOR PREPARATION THEREOF

This application is a National Stage Application of PCT/IB2016/057530, filed 12 Dec. 2016, which claims benefit of Serial No. 6681/CHE/2015, filed 12 Dec. 2015 in India and which applications are incorporated herein by reference. To the extent appropriate, a claim of priority is made to each of the above-disclosed applications.

FIELD OF THE INVENTION

The present invention relates to effervescent compositions of Metformin and fixed dose combinations thereof.

BACKGROUND OF THE INVENTION

Approximately an estimated 387 million people worldwide have Type 1 or Type-2 diabetes. Type-2 diabetes is the most common type, accounting for an estimated 90 to 95 percent of all diagnosed adult diabetes cases in the United States.

Metformin in an immediate release form is approved in the USA as Glucophage® and in the extended release form as Glucophage XR® and Glumetza®. However, treatment with Metformin compositions presents some challenges. Firstly, in the presence of normal renal function, there are no differences between single- or multiple-dose pharmacokinetics of Metformin between patients with Type-2 diabetes and normal subjects, nor is there any accumulation of Metformin in either group at usual clinical doses. However, limited data from controlled pharmacokinetic studies of GLUCOPHAGE® in healthy elderly subjects suggested that total plasma clearance of Metformin is decreased, the half-life is prolonged, and Cmax is increased, compared to healthy young subjects. From these data, it appears that the change in Metformin pharmacokinetics with aging is primarily accounted for by a change in their renal function. Thus a reduction in dose is necessary for such cases where the renal function is decreased. Secondly, a population of patients suffering from Type-2 diabetes is elderly people, pediatric patients and people with dysphagia. Due to the high dose (500-1000 mg) of Metformin available in the form of tablets having a size of 19 mm×10.5 mm; oral administration of Metformin is difficult in these patients. A suitable alternative for such patients is administration of Metformin in the form of a solution. A solution of Metformin is approved as Riomet®. But such a solution or liquid dosage form has its own disadvantages like, larger bulk of the dosage form and faster loss of potency as compared to solid dosage forms. Moreover, Metformin is a bitter drug and has side effects like abdominal or stomach discomfort. Therefore, there is a necessity to administer Metformin as a taste-masked or tasteless composition with excipients that could act as a buffer and are capable of mediating the pH of a patient's stomach from 15 to 30 minutes up to about 1 hour Fourthly, it is desirable to provide a Metformin containing composition having low mineral content, particularly that of sodium and potassium. Excess potassium intake can cause dangerous heartbeat irregularities and even sudden death in patients with Type-2 diabetes having a co-morbid cardiovascular disease or in diabetic patients at risk of developing a cardiovascular disease; while a sodium-restricted diet has long been a first line of intervention for people with hypertension and is particularly important in those with Type-2 diabetes.

Finally, besides having a high dose, Metformin is hygroscopic and has poor compactibility. Binders are known to improve the flowability and compactability of Metformin granulates. However, binders also increase the disintegration time of solid dosage forms. A Metformin composition free of an affirmatively added binder which would rapidly disintegrate is thus preferred, but would be highly challenging to develop. Studies have shown that many patients with Type-2 diabetes do not achieve optimal glycemic control, and progression of diabetes over time requires more than one pharmacotherapy to achieve the glycemic goal. Following are the approved fixed-dose combinations in USA containing Metformin: Avandamet®, Glucovance®, Actoplus Met®, Metaglip®, Prandimet®, Janumet®, Invokamet®, Jentadueto®, Kazano®, Synjardy®, Kombiglyze® XR, Actoplus Met® XR, Fortamet®, Xigduo® XR, Janumet® XR.

Most of these approved compositions are available only with a Metformin content of 500 mg and 1000 mg and therefore present the same challenges enumerated above for Metformin. Therefore, there is also a need in the art to provide compositions of Metformin alone and in combination with other antidiabetic agents which can overcome the challenges associated with Metformin therapy. At the same time, these compositions should be able to be manufactured easily by a cost-effective process. It is preferable that such a manufacturing process be continuous and result into compositions which maintain their integrity over their shelf life.

It has now been surprisingly found that effervescent compositions of the present invention can overcome the aforementioned challenges of anti-diabetic therapy with Metformin and its combinations.

SUMMARY OF THE INVENTION

According to an aspect of the present invention there is provided an effervescent composition comprising Metformin, an acid, a base and optionally, one or more anti-diabetic agents or one or more pharmaceutically acceptable excipients, wherein the composition has a retained carbon dioxide content of at least 90% of the input blend.

According to another aspect of the present invention there is provided a process of preparing effervescent composition comprising the steps of:
a) Processing an acid and a base through a twin screw processor; or
b) Processing an acid, a base and Metformin or at least one pharmaceutically acceptable salt thereof, optionally with at least one other anti-diabetic agent through a twin screw processor;
c) Mixing the product of step a) with Metformin or at least one pharmaceutically acceptable salt thereof, and optionally at least one other anti-diabetic agent, and optionally at least one excipient followed, by compressing into tablets or filling into capsules or sachets; or
d) Compressing the product of step b) into tablets or filling it into capsules or sachets; after optionally mixing with at least one other anti-diabetic agent or at least one excipient;
wherein only a portion of acid is melted in Step (a) or Step (b) to serve as an in-situ granulating agent and the said process being free of affirmatively added binders and granulating solvents.

DETAILED DESCRIPTION OF THE INVENTION

The present invention relates to effervescent compositions of Metformin and fixed dose combinations thereof.

The present invention provides effervescent compositions comprising Metformin and optionally at least one other anti-diabetic agent that quickly dissolve on addition to water to give a sparkling solution with good taste which masks the bitter taste of Metformin and enables administration to children, elderly patients and patients with dysphagia. Being buffered solutions, these compositions also overcome the side effects of abdominal or stomach discomfort associated with Metformin therapy. These effervescent compositions are prepared by a novel process, which results in maximum retention of carbon dioxide after processing.

The effervescent compositions can be provided in unit dosage forms, which are easy to carry, stable over their shelf-life and are also suitable for tailoring of dosing regimen of a patient in need thereof.

The present invention is capable of offering a variety of fixed dose combinations of Metformin with the actives of the aforementioned marketed preparations, in the form of effervescent compositions. The Metformin combinations of the present invention are capable of delivering Metformin from 250 mg to 1000 mg to the Type-2 diabetes patients and can be also used by physicians to tailor individualized treatment regimens for Type-2 diabetes patients.

In an aspect of the present invention, there is provided an effervescent composition comprising Metformin from 1 to 100% by weight; preferably 10 to 40% by weight of the composition.

In another aspect of the present invention, there is provided a method for treating Type-2 diabetes, in a patient in need thereof comprising administering to the patient an effervescent Metformin composition.

In yet another aspect of the present invention, there is provided use of an effervescent Metformin composition in the treatment of Type-2 diabetes.

In an embodiment, the present invention relates to an effervescent composition comprising Metformin.

In another embodiment, the present invention relates to an effervescent composition comprising Metformin and at least one other anti-diabetic agent.

The term "effervescent composition" as used herein refers to any composition which, on contact with water, liberates carbon dioxide and can include, but is not limited to granules, granules filled into sachets, tablets, capsules and the like.

The term "Metformin" as used herein includes Metformin and pharmaceutically acceptable salts, esters or derivatives. Metformin hydrochloride is the preferred salt, which is the reason for describing the invention with reference to Metformin hydrochloride, although it must not be considered to be limited only to the use of Metformin hydrochloride.

The term "other anti-diabetic agent" as used herein includes, but is not limited to, sulfonylureas, thiazolidinediones, meglitinides, sodium-glucose co-transporter 2 (SGLT2) inhibitors, alpha-glucosidase inhibitors and DPP-IV inhibitors and pharmaceutically acceptable salts, free base forms, free acid form, esters or derivatives thereof. A few non-limiting examples of these classes of drugs are Rosiglitazone Maleate, Glyburide, Pioglitazone Hydrochloride, Glipizide, Glimepiride, Repaglinide, Sitagliptin Phosphate, Canagliflozin, Linagliptin, Alogliptin Benzoate, Empagliflozin, Saxagliptin Hydrochloride, Vildagliptin, Teneligliptin, Pioglitazone Hydrochloride and Dapagliflozin Propanediol or their derivatives or alternative salts thereof.

The term "input blend" or "pre mix" as used herein, means the material that is fed into the twin screw processor for processing. It includes an acid, a base, Metformin and/or one or more other anti-diabetic agents, and optionally other excipients.

The terms "acid component" and "acid" are used as alternatives to each other. Similarly, the terms "base component" and "base" are used as alternatives to each other, throughout the specification.

In an embodiment, the present invention provides an effervescent composition comprising Metformin, an acid and a base, wherein the composition has retained carbon dioxide content of at least 90% of the input blend.

In an embodiment, the present invention provides an effervescent composition comprising Metformin, at least one other anti-diabetic agent, an acid and a base, wherein the composition has retained carbon dioxide content of at least 90% of the input blend.

The retained carbon dioxide content (%) is a measure of the quality of effervescence that would be exhibited by the effervescent composition. It is a relative measurement of the amount of $CO_2$ in the finished product compared to the amount of $CO_2$ present in the input blend. Accordingly, 90% retention of carbon dioxide by the composition means that there has been only a 10% loss of carbon dioxide during the process for preparation of the composition. It suggests that the composition will exhibit a stronger effervescence as compared to a composition with 50% carbon dioxide retention. Measurement of $CO_2$ retention is more elaborately explained in the examples.

The effervescent compositions of the present invention essentially comprise an acid and a base. In accordance with an embodiment, the acid can be selected from one or more of organic acids in the form of free acid, acid anhydride or its salt form. Specifically, the acid can be selected from but not limited to citric acid, tartaric acid, fumaric acid, malic acid, adipic acid, succinic acid, lactic acid, glycolic acid, alpha hydroxy acid, ascorbic acid, amino acid. For example, in some embodiments, the acid is citric acid.

In accordance with an embodiment of the present invention, the base is a carbon dioxide precursor and can be selected from but not limited to one or more of carbonate-containing compounds, such as carbonate, sesquicarbonate or bicarbonate salts of potassium, lithium, sodium, calcium, or ammonium; L-lysine carbonate; arginine carbonate; sodium glycine carbonate; or sodium amino acid carbonate. Mixtures of one or more bases can also be used. For example, in some embodiments, the base is a mixture of sodium carbonate and sodium bicarbonate or a mixture of sodium carbonate and potassium bicarbonate or a mixture of potassium bicarbonate and potassium carbonate or a mixture of sodium bicarbonate and potassium carbonate.

In accordance with an exemplary embodiment, an anhydrous form of the acid is used. In accordance with an exemplary embodiment, an anhydrous form of the base is used. In yet another embodiment, both an anhydrous acid and an anhydrous base can be used.

The amount of the acid and the base in the effervescent compositions can vary depending on the acid and the base used. The acid and base can be present in a molar ratio ranging from 3:1 to 1:5, preferably from 1:2.5 to 1:3.5. In exemplary embodiments, the weight ratio of the acid and the base can be selected from 1:1.1-1:1.53. Sodium and/or potassium levels are therefore kept well within the total daily intake recommended for such minerals.

One or more excipients can optionally be included in the effervescent compositions either intragranularly or extragranularly or as a combination. Suitable excipients are selected from a group including, but not limited to, fillers, disintegrants, surfactants, taste modifiers, soluble and insoluble lubricants, flavoring substances, coloring agents, sweeteners or combinations thereof.

Suitable fillers include, but are not limited to, starch, mannitol, sorbitol, lactose, microcrystalline cellulose and combinations or co-agglomerates thereof. The amount of the filler in the composition can be from about 1-30% w/w, preferably about 2-20% w/w of the composition.

Suitable disintegrants include, but are not limited to, natural, modified or pregelatinized starch, crospovidone, croscarmellose sodium, sodium starch glycolate, low-substituted hydroxypropyl cellulose, crospovidone, calcium silicate and starch or mixtures thereof. The amount of the disintegrant in the composition can be from about 2-10% w/w, preferably 2-7% w/w of the composition.

Suitable surfactants include, but are not limited to, sodium docusate, polyoxyethylene sorbitan fatty acid ester, sodium lauryl sulfate, sorbic acid, sorbitan fatty acid ester, and mixtures thereof. The amount of the surfactant in the composition can be from about 1-10% w/w, preferably 1-5% w/w of the composition.

Suitable taste modifiers include, but are not limited to, ion exchange resins which are either strong or weak cation or anion exchangers which form a resin complex with the drug, oils, surfactants, polyalcohols, lipids, lecithins, salts of metals (such as sodium chloride, sodium acetate, sodium gluconate), amino acids such as glycine, taurine, alanine, adsorbents (such as magnesium aluminium silicate, zeolite®, silica, clay). The compositions may also include salivating agents including, but not limited to, micronized polyethylene glycol, sodium chloride or precipitated micronized silica. The amount of the taste modifier in the composition can be from about 1-10% w/w, preferably 1-5% w/w of the composition.

Suitable sweeteners include, but are not limited to acesulfame potassium, aspartame, saccharin, sucralose, neotame, advantame, sucrose and combinations thereof. The amount of the sweetener in the composition can be from about 0.25-10% w/w, preferably 0.25-5% w/w of the composition.

Suitable soluble lubricants include, but are not limited to, polyethylene glycols (PEG), for example-PEG 4000, PEG 6000 and PEG 8000, polyoxyethylene stearate and sodium or magnesium lauryl sulphate, sodium benzoate, potassium sorbate, L-leucine and the like and combinations thereof. Insoluble lubricants can include, but are not limited to, magnesium stearate, stearic acid, glyceryl palmitostearate, sodium stearyl fumarate and the like and combinations thereof. The amount of the lubricant in the composition can be from 0.1% to 5% w/w, preferably from 1.5% to 4.5% w/w of the composition.

Suitable flavoring substances include, but are not limited to, natural flavors such as natural oils, extracts from plants, leaves, flowers, fruits and so forth and artificial flavors such as synthetic flavor oils and flavoring aromatics and so forth and combinations thereof. These may include but are not limited to cinnamon oil, oil of wintergreen, peppermint oil, clove oil, bay oil, anise oil, eucalyptus, thyme oil, cedar leaf oil, oil of nutmeg, oil of sage, oil of bitter almonds, cassia oil and the like. Also useful as flavors are vanilla, citrus oil, including lemon, orange, grape, lime and grapefruit, and fruit essences, including apple pear, peach, strawberry, raspberry, cherry, plum, pineapple, apricot and so forth. Flavors which have been found to be particularly useful include but are not limited to commercially available orange, lemon, grape, cherry and bubble gum flavors and mixtures thereof. The amount of flavoring may depend on a number of factors, including the organoleptic effect desired. The amount of the flavoring substance in the composition can be from about 0.01% to 10% w/w, preferably from 0.01% to 5% w/w of the composition.

Useful coloring agents include but are not limited to food, drug and cosmetic (FD&C) colors, for example—dyes, pigments, lakes, natural colorants and derived colorants. Useful lakes include dyes adsorbed on aluminum hydroxide and other suitable carriers. Examples of suitable colors include FD&C Red No. 3, FD&C Red No. 40, FD&C Blue No. 1, FD&C Blue No. 2, FD&C Yellow No. 5, FD&C Yellow No. 6, FD&C Green No. 3 and combinations thereof. The amount of coloring agent depends on the aesthetic appearance desired and is well known to those skilled in the art.

In an embodiment, the present invention provides a taste-masked effervescent composition comprising Metformin, at least one sweetener or flavor, an acid, a base and optionally, at least one other anti-diabetic agent; wherein the composition has retained carbon dioxide content of at least 90% of the input blend.

In an embodiment, the present invention provides a taste-masked effervescent composition comprising Metformin, optionally, at least one other anti-diabetic agent, an acid and a base, wherein the composition has retained carbon dioxide content of at least 90% of the input blend and is stable over its shelf life.

In an embodiment, the present invention provides an effervescent Metformin composition comprising:
  i. Metformin or at least one pharmaceutically acceptable salt thereof;
  ii. An anhydrous acid component comprising a combination of a portion of the acid that has been melted and a portion of the acid that has not been melted;
  iii. An anhydrous base component comprising a carbonate functional group, wherein the base component is capable of reacting with the acid component to form carbon dioxide; and
  iv. Optionally at least one other anti-diabetic agent;
Wherein the anhydrous acid component and the anhydrous base component are present in a weight ratio ranging from 3:1 to 1:5 and the composition is free of affirmatively added binders and granulating solvents.

In an embodiment, the present invention provides an effervescent composition comprising Metformin, an acid and a base, wherein the composition has retained carbon dioxide content of at least 90% of the input blend, and wherein the process for preparation of the composition involves the use of a twin screw processor.

In an embodiment, the present invention provides an effervescent composition comprising Metformin, at least one other anti-diabetic agent, an acid and a base, wherein the composition has retained carbon dioxide content of at least 90% of the input blend, and wherein the process for preparation of the composition involves the use of a twin screw processor.

The co-rotating twin-screw processor has two co-rotating screws inside a processor barrel. These screws are open length wise, and closed cross wise. The co-rotating twin screw processor has a modular design for barrels and screws. Segmented screws convey and shear the materials in channels bounded by screw flights and barrel walls, with short mass transfer distances. Each individual screw section is designed to perform specific functions such as conveying, mixing, shearing, or pressure building, thus allowing precise control of conditions along the screw length. The screw elements differ in pitch, pitch direction, length, and angle of offset. Pitch, length, and location of such screw elements on the shaft define a screw profile that influences the product characteristics. Due to variable screw configuration, twin screw processor provides greater flexibility of operations to control characteristics of product by monitoring and regulating residence time, product temperature, pressure, and shear. The processing aspects and parameters related to processing of granulating blend in a twin screw processor are elaborately explained in the examples. Also, the co-pending Indian patent application 4527/CHE/2014 which discloses methods and systems for processing granulation blend in a twin screw processor is incorporated herein by reference.

In the twin screw processor, there is melting of only a portion of the acid. This leads to formation of solid bridges with particles of co-processed materials. These bridges lead to binding of the particles, in close proximity, to form deformable, irregular shaped, porous granules that have improved compressibility.

As little or no reaction takes place between the acid and the base during processing in the twin screw processor, negligible or no carbon dioxide is lost during the process. Therefore, the granules retain substantially all of the carbon dioxide content of the input blend that is fed into the twin screw processor. This leads to improved effervescence when exposed to water.

Further, as the acid and base are in close proximity, the granules formed according to the present invention exhibit improved mechanical strength. As would be evident from the examples, the tablets formed from granules exhibit improved hardness. The formation of porous effervescent compositions having porosity at least 50% greater than the porosity of the input blend that is fed into the twin screw processor, using an in-situ granulating agent in the form of a meltable acid, results in avoiding the use of aqueous or non-aqueous solvents or affirmatively added binders. This in-situ granulation process therefore successfully eliminates the requirement of adding moisture for processing of input blend fed into the processor and the temperature of the barrels of the twin screw processor leads to evaporation of the moisture that may be generated during granulation. Therefore, the moisture content of the granules can be as low as below 1%.

Granules comprising acid and base are prepared using the twin screw processor and Metformin and optionally, the other anti-diabetic agent are subsequently mixed homogenously with the granules i.e. extragranularly or alternatively, Metformin and optionally the other anti-diabetic agent are processed in the twin screw processor along with the acid and base to incorporate them within the effervescent granules i.e. intragranularly. Another variant of the process is to co-process Metformin and the other anti-diabetic agent, separately with the acid and the base through the twin screw processor to obtain two separate set of granules that is mixed in suitable proportions, to form a blend that is compressed into tablets or filled into capsules or sachets.

In an embodiment, the present invention provides a process for preparation of placebo effervescent granules having compressibility index between 20-30% and retained carbon dioxide content of at least 90% of the input blend comprising the step of granulating a mixture comprising an acid and a base in a twin screw processor, in the absence of aqueous and non-aqueous solvents and an affirmatively added binder to obtain granules.

In an embodiment, the present invention provides a process for preparation of effervescent granules comprising Metformin and optionally at least one other anti-diabetic agent; having compressibility index between 20-30% and retained carbon dioxide content of at least 90% of the input blend comprising the step of granulating a mixture comprising an acid, a base, Metformin and optionally at least one other anti-diabetic agent, in a twin screw processor, in the absence of aqueous and non-aqueous solvents and an affirmatively added binder, to obtain granules.

In an embodiment, the present invention provides effervescent granules comprising Metformin, an acid and a base and optionally at least one other anti-diabetic agent, wherein the effervescent granules have retained carbon dioxide content of at least 90% of the input blend, and wherein the granules do not contain an affirmatively added binder.

In an embodiment, the present invention provides an effervescent composition comprising Metformin, an acid and a base and optionally at least one other anti-diabetic agent, wherein the effervescent composition has retained carbon dioxide content of at least 90% of the input blend, and wherein the composition does not contain an affirmatively added binder.

In an embodiment, the present invention provides effervescent granules comprising Metformin, an acid and a base and optionally at least one other anti-diabetic agent, wherein the effervescent granules have retained carbon dioxide content of at least 90% of the input blend, do not contain an affirmatively added binder and have a porosity at least 50% greater than the porosity of input blend.

In an embodiment, the present invention provides a process for preparation of an effervescent Metformin composition comprising the steps of:

a) Processing an acid and a base through a twin screw processor; or b) Processing an acid, a base and Metformin or at least one pharmaceutically acceptable salt thereof, optionally with at least one other anti-diabetic agent through a twin screw processor;

c) Mixing the product of step a) with Metformin or at least one pharmaceutically acceptable salt thereof, and optionally at least one other anti-diabetic agent, and optionally at least one excipient followed, by compressing into tablets or filling into capsules or sachets; or d) Compressing the product of step b) into tablets or filling it into capsules or sachets; after optionally mixing with at least one other anti-diabetic agent or at least one excipient;

wherein only a portion of acid is melted in Step (a) or Step (b) to serve as an in-situ granulating agent and the said process being free of affirmatively added binders and granulating solvents.

In accordance with an embodiment, the effervescent tablet compositions of the present invention exhibit a disintegration time of less than 3 minutes, preferably less than 60 seconds (secs) in water at room temperature of about 25° C.±5° C.

In an embodiment, the present invention provides an effervescent composition comprising Metformin, an acid and a base, wherein the composition has retained carbon dioxide content of at least 90% of the input blend, wherein the composition has a disintegration time of less than 3 minutes in water, and wherein the process for preparation of the composition involves the use of a twin screw processor and does not involve the use of aqueous solvents, non-aqueous solvents and an affirmatively added binder.

In an embodiment, the present invention provides an effervescent composition comprising Metformin, at least one other anti-diabetic agent, an acid and a base, wherein the composition has retained carbon dioxide content of at least 90% of the input blend, wherein the composition has a disintegration time of less than 3 minutes in water at room temperature, and wherein the process for preparation of the composition involves the use of a twin screw processor and does not involve the use of aqueous solvents, non-aqueous solvents and an affirmatively added binder.

Any conventional compression techniques well known to the person skilled in the art may be used to prepare the effervescent tablets of the present invention.

In accordance with an embodiment, the tablet compositions of the present invention have a hardness of at least 2 kp (kilopond). In accordance with an exemplary embodiment, the tablets have a hardness of 2 to 25 kp.

The following brands which include Metformin or Metformin combinations with other anti-diabetic agents are indicated for the treatment of Type-2 diabetes:

or LOD), retained $CO_2$ content, compressibility, hardness, bulk density and tap density of the compositions formed in accordance with embodiments of the present disclosure.

Determination of Moisture Content (LOD): The input blend or pre mix fed into the twin screw processor, and the granules were analyzed by an infrared moisture balance analyzer, Sartorius MA150, at 75° C. for 5 minutes. Loss in weight was recorded as percent (%) moisture content with respect to their initial weight.

Determination of Retained $CO_2$ Content: 5.0 g of input blend or pre mix fed into the twin screw processor, or granules or 5 tablets were added into separate 100 ml 2N sulfuric acid solutions. The loss in weight of the input blend or granules or tablets due to liberation of $CO_2$ as a result of the reaction between sulfuric acid and bicarbonate or carbonate present in the input blend or granules or the tablets was recorded as observed weight of carbon dioxide. The difference between the weight of the input blend and granules after reaction and the initial weight of input blend and granules respectively was also calculated to measure the retained $CO_2$ content (g) in the blend or granules or the tablet. The percent (%) retained $CO_2$ content in the granules or the tablet was then calculated using the formula below:

TABLE 1

Brands which include Metformin or Metformin combinations with other anti-diabetic agents

| Brand | Source of label information (Retrieved from the Internet: Nov. 18, 2015) |
| --- | --- |
| ACTOPLUS MET ® | http://www.accessdata.fda.gov/drugsatfda_docs/label/2014/021842s019lbl.pdf |
| ACTOPLUS MET ® XR | http://www.accessdata.fda.gov/drugsatfda_docs/label/2013/022024s001lbl.pdf |
| AVANDAMET ® | http://www.accessdata.fda.gov/drugsatfda_docs/label/2014/021410s036s037s038lbl.pdf |
| FORTAMET ® | http://www.accessdata.fda.gov/drugsatfda_docs/label/2008/021574s010lbl.pdf |
| GLUCOPHAGE ® and GLUCOPHAGE ® XR | http://www.accessdata.fda.gov/drugsatfda_docs/label/2008/020357s031,021202s016lbl.pdf |
| GLUCOVANCE ® | http://www.accessdata.fda.gov/drugsatfda_docs/label/2013/021178s015lbl.pdf |
| GLUMETZA ® | http://www.accessdata.fda.gov/drugsatfda_docs/label/2011/021748s010lbl.pdf |
| INVOKAMET ® | http://www.accessdata.fda.gov/drugsatfda_docs/label/2015/204353s003lbl.pdf |
| JANUMET ® | http://www.accessdata.fda.gov/drugsatfda_docs/label/2015/022044s035lbl.pdf |
| JANUMET ® XR | http://www.accessdata.fda.gov/drugsatfda_docs/label/2015/202270s010lbl.pdf |
| JENTADUETO ® | http://www.accessdata.fda.gov/drugsatfda_docs/label/2015/201281s010lbl.pdf |
| KAZANO ® | http://www.accessdata.fda.gov/drugsatfda_docs/label/2015/203414s005lbl.pdf |
| KOMBIGLYZE ® XR | http://www.accessdata.fda.gov/drugsatfda_docs/label/2015/200678s016lbledt.pdf |
| METAGLIP ® | http://www.accessdata.fda.gov/drugsatfda_docs/label/2013/021460s010lbl.pdf |
| PRANDIMET ® | http://www.accessdata.fda.gov/drugsatfda_docs/label/2012/022386s000lbl.pdf |
| RIOMET ® | http://www.accessdata.fda.gov/drugsatfda_docs/label/2014/021591s008lbl.pdf |
| SYNJARDY ® | http://www.accessdata.fda.gov/drugsatfda_docs/label/2015/206111lbl.pdf |
| XIGDUO ® XR | http://www.accessdata.fda.gov/drugsatfda_docs/label/2014/205649s000lbl.pdf |

The information from labels available on the URLs mentioned in the table 1 above, in particular, information such as, dosage regimen and indications, is incorporated herein, by reference.

As per present invention, any of the above embodiments can be used in the treatment of Type-2 diabetes mellitus.

In an embodiment, the present invention provides a method for treating Type-2 diabetes, in a patient in need thereof comprising administering to the patient an effervescent composition, as per any of the embodiments mentioned above.

In another embodiment, the present invention provides use of an effervescent composition, as per any of the embodiments mentioned above, in the treatment of Type-2 diabetes.

The present invention is exemplified by the following non-limiting examples.

EXAMPLES

Described herein are exemplary processes for determining the moisture content (also referred to as Loss on Drying Retained $CO_2$ content (%)=(Observed Weight (g) of $CO_2$ in granules or tablets×100)/Observed Weight (g) of $CO_2$ in input blend Determination of Hardness and Thickness of the Tablet: The hardness was calculated as the average of the hardness measured using Inweka TBH 125 hardness tester (Germany) for each of five tablets (number of units tested, n=5). The thickness was calculated as the average of the thickness measured using vernier callipers for each of 5 tablets (number of units tested, n=5).

Measurement of Bulk and Tap Density: A known amount (m) of the input blend and the granules were added into two separate dry graduated 100 ml cylinders. The contents of the two cylinders were leveled without compacting; and the unsettled apparent bulk volume ($V_0$) to the nearest graduated unit was read.

The bulk density (g/ml) was calculated using formula:

Bulk Density=Mass (m)/Bulk Volume ($V_0$)

To calculate the tap density, the contents of the two cylinders were tapped mechanically up to a maximum of 1250 taps and the apparent tapped volume ($V_t$) to the nearest graduated unit was read. The tap density was calculated using formula: Tap Density=Mass (m)/Tapped Volume ($V_t$)

Measurement of porosity: Porosity was measured in terms of percentage relative bulk porosity and percentage relative tap porosity.

Percentage relative bulk porosity can be calculated considering 1 g specific (Sp) volume using formula:

% Relative Bulk Porosity=((Bulk Sp. volume of 1 g granule−Bulk Sp. volume of 1 g input blend)×100)/Bulk Sp. volume of 1 g input blend Where, Bulk Sp. volume of 1 g granule=1/Bulk density of granules; and Bulk Sp. volume of 1 g input blend=1/Bulk density of input blend Percentage relative tap porosity was calculated considering 1 g specific (Sp) volume using formula:

% Relative Tap Porosity=((Tap Sp. volume of 1 g granule−Tap Sp. volume of 1 g input blend)×100))/Tap Sp. volume of 1 g input blend Where, Tap Sp. volume of 1 g granule=1/Tap density of granules Tap Sp. volume of 1 g input blend=1/Tap density of input blend Measurement of Compressibility: Compressibility was measured in terms of Hausner ratio and Compressibility Index, as provided in Hausner, H. H., Int. J. Powd. Metall, Vol 3, pg 7, 1967 and Can, R. L., Chem. Eng., Vol 72, Issue 1, pg 163 and Issue 2, pg 69, 1965, respectively. Both the citations are incorporated herein by reference.

The invention is further illustrated by the following examples which are provided to exemplify the invention, and do not limit the scope of the invention. While the present invention has been described in terms of its specific embodiments, certain modifications and equivalents will be apparent to those skilled in the art, and are intended to be included within the scope of the present invention.

Example 1

Metformin Hydrochloride Effervescent Granules

TABLE 2

Quantitative composition of Metformin hydrochloride effervescent granules

| Ingredients | % w/w |
|---|---|
| Metformin HCL | 12.55 |
| Citric acid anhydrous | 38.96 |
| Sodium bicarbonate | 43.97 |
| Sodium carbonate | 4.52 |
| Total | 100 |

Manufacturing Process:

Metformin hydrochloride was dried at 45° C. for 1 hour and passed through #60 mesh. Citric acid anhydrous, sodium bicarbonate and sodium carbonate were deagglomerated and dried at 45° C. for 3 hours and then weighed accurately as per the formula. Metformin hydrochloride, citric acid anhydrous, sodium bicarbonate and sodium carbonate were blended and immediately processed in a co-rotating twin screw processor (Machine: Omega 20, L/D: 30) at processing area relative humidity (RH) of 20%±5%RH and at a processing area temperature of 30° C.±2° C. The process was performed at screw speed of 600 rpm and feed rate of 186 g/min.

TABLE 3

Screw configuration for Example 1

| Elements | | | | | | | |
|---|---|---|---|---|---|---|---|
| RSE 15/15 | NRF 40/20 | RFV 40/40 | RFN 40/20 | RSE 30/15 | RSE 15/30 | RSE 15/15 | RSE 20/20 |
| No's 1 | 1 | 4 | 1 | 1 | 8 | 7 | 1 |

List of Abbreviations for Elements

RSE Right Handed Screw Element

RFV Regular Flight Shovel Element

RFN Regular Flight Shovel Element to Normal

NRF Normal to RFV (transition element)

TABLE 4

Barrel temperature profile (° C.) for Example 1

| B1 | B2 | B3 | B4 | B5 |
|---|---|---|---|---|
| 30 | 30 | 140 | 140 | 140 |

TABLE 5

Parameters for pre mix and granules of Example 1

| Parameters | Pre mix | Granules |
|---|---|---|
| Loss on drying (75° C. for 5 minutes) | 0.15% | 0.05% |
| Retained Carbon dioxide content (%) | — | 94.53 |
| Bulk density (g/cc) | 0.84 | 0.48 |
| Tapped density (g/cc) | 1.21 | 0.65 |
| Compressibility index (%) | 30.77 | 25.30 |
| Hausner's ratio | 1.44 | 1.340 |
| Median diameter (microns) | 180 | 600 |
| Angle of repose (degrees) | — | 22.14 |

Note:
Retained Carbon dioxide content (%) of granules is reported in comparison to pre mix.

TABLE 6

Quantitative compositions of Metformin for Examples 2-4

| Ingredients | Ex 2 Metformin HCL 500 mg | | Ex 3 Metformin HCL 500 mg + Sitagliptin 50 mg | | Ex 4 Metformin HCL 500 mg + Saxagliptin 5 mg | |
| --- | --- | --- | --- | --- | --- | --- |
| | % w/w | mg/tablet | % w/w | mg/tablet | % w/w | mg/tablet |
| Metformin HCL granules | 97.42 | 4000 | 95.96 | 4000 | 97.27 | 4000 |
| Sitagliptin Phosphate | | | 1.5 | 62.53 | | |
| Saxagliptin HCL monohydrate | | | | | 0.15 | 6.14 |
| Strawberry flavour | 0.05 | 2 | 0.05 | 2 | 0.05 | 2 |
| Sucralose | 0.58 | 24 | 0.57 | 24 | 0.58 | 24 |
| Sodium benzoate | 1.95 | 80 | 1.92 | 80 | 1.94 | 80 |
| Total | 100 | 4106 | 100 | 4168 | 100 | 4112 |

Example 2

Metformin Hydrochloride 500 mg Tablet

Manufacturing Process:

Metformin hydrochloride granules (as per Example 1) were passed through #16 mesh sieve, mixed with sucralose and strawberry flavour that were passed through #60 mesh sieve, and then finally lubricated with sodium benzoate passed through #100 mesh sieve. This mixture was compressed using a rotary tablet compression machine (Machine: Riddi Pharma rotary press) using 25 mm round flat face beveled edge tooling.

Example 3

Effervescent Tablets of Metformin Hydrochloride 500 mg and Sitagliptin 50 mg

Manufacturing Process:

Metformin hydrochloride granules (as per Example 1), were passed through #16 mesh sieve, mixed with Sitagliptin phosphate, sucralose and strawberry flavour that were all passed through #60 mesh sieve, and then finally lubricated with sodium benzoate passed through #100 mesh sieve. This mixture was compressed using a rotary tablet compression machine (Machine: Riddi Pharma rotary press) using 25 mm round flat face beveled edge tooling.

Example 4

Effervescent Tablets of Metformin Hydrochloride 500 mg and Saxagliptin

Manufacturing Process:

Metformin hydrochloride granules (as per Example 1), were passed through #16 mesh sieve, mixed with Saxagliptin hydrochloride monohydrate, sucralose and strawberry flavour that were all passed through #60 mesh sieve, and then finally lubricated with sodium benzoate passed through #100 mesh sieve. This mixture was compressed using a rotary tablet compression machine (Machine: Riddi Pharma rotary press) using 25 mm round flat face beveled edge tooling.

Example 5

Metformin Hydrochloride 500 mg and Sitagliptin 50 mg Granules

TABLE 7

Quantitative compositions of Metformin for Examples 5-6

| Ingredients | Ex 5 Metformin HCL + Sitagliptin granules | Ex 6 Metformin HCL 500 mg + Sitagliptin 50 mg | |
| --- | --- | --- | --- |
| | % w/w | % w/w | mg/tablet |
| Metformin HCL | 12.55 | — | — |
| Metformin HCL and Sitagliptin granules | — | 97.42 | 4000 |
| Sitagliptin Phosphate | 1.56 | — | — |
| Citric acid anhydrous | 38.25 | — | — |
| Sodium bicarbonate | 43.19 | — | — |
| Sodium carbonate | 4.44 | — | — |
| Strawberry flavour | — | 0.05 | 2 |
| Sucralose | — | 0.58 | 24 |
| Sodium benzoate | — | 1.95 | 80 |
| Total | 100 | 100 | 4106 |

Manufacturing Process:

Metformin hydrochloride and Sitagliptin phosphate were dried at 45° C. for 1 hour and passed through #60 mesh sieve and weighed accurately as per the formula. Citric acid anhydrous, sodium bicarbonate and sodium carbonate were deagglomerated and dried at 45° C. for 3 hours and then weighed accurately as per the formula. Metformin hydrochloride, Sitagliptin phosphate, citric acid anhydrous, sodium bicarbonate and sodium carbonate were blended and immediately processed in a co-rotating twin screw processor (Machine: Omega 20, L/D: 30) at processing area relative humidity of 20%±5% RH and temperature of 30° C.±2° C. The process was performed at screw speed of 600 rpm and feed rate of 347.46 g/min.

TABLE 8

Screw configuration for Example 5

| Elements | | | | | | | |
|---|---|---|---|---|---|---|---|
| RSE 15/15 | NRF 40/20 | RFV 40/40 | RFN 40/20 | RSE 30/15 | RSE 15/30 | RSE 15/15 | RSE 20/20 |
| No's 1 | 1 | 4 | 1 | 1 | 8 | 7 | 1 |

TABLE 9

Barrel temperature profile (° C.) for Example 5

| B1 | B2 | B3 | B4 | B5 |
|---|---|---|---|---|
| 30 | 30 | 140 | 140 | 140 |

TABLE 10

Parameters for pre mix and granules of Example 5

| Parameters | pre mix | Granules |
|---|---|---|
| Loss on drying (75° C. for 5 minutes) | 0.09% | 0.15% |
| Retained Carbon dioxide content (%) | — | 92.16 |
| Bulk density (g/cc) | 0.86 | 0.526 |
| Tapped density (g/cc) | 1.11 | 0.728 |
| Compressibility index (%) | 22.47 | 27.78 |
| Hausner's ratio | 1.29 | 1.35 |
| Median diameter (microns) | 180 | 300 |
| Angle of repose (degrees) | — | 21.47 |

Note:
Retained Carbon dioxide content (%) of granules is reported in comparison to pre mix.

Example 6

Metformin Hydrochloride 500 mg and Sitagliptin 50 mg Tablets

Manufacturing Process:

Metformin Hydrochloride & Sitagliptin effervescent granules (as per Example 5), were passed through #16 mesh sieve, mixed with sucralose and strawberry flavour that were passed through #60 mesh sieve, and then finally lubricated with sodium benzoate passed through #100 mesh sieve. This mixture was compressed using a rotary tablet compression machine (Machine: Riddi Pharma rotary press) using 25 mm round flat face beveled edge tooling.

Example 7

Placebo Effervescent Granules Using Potassium Bicarbonate

TABLE 11

Quantitative composition of placebo potassium bicarbonate granules

| Ingredients | Ex 7 % w/w |
|---|---|
| Citric acid anhydrous | 38.99 |
| Potassium bicarbonate | 61 |
| Total | 100 |

Manufacturing Process:

Citric acid anhydrous and potassium bicarbonate were deagglomerated and dried individually at 45° C. for 3 hours and then weighed accurately as per the formula. Citric acid anhydrous and potassium bicarbonate were blended and immediately processed in a co-rotating twin screw processor (Machine: Omega 20, L/D: 30) at a screw speed of 600 rpm and a feed rate of 228 g/min at processing area relative humidity of 20%±5%RH and processing area temperature of 30° C.±2° C.

TABLE 12

Screw configuration for Example 7

| Elements | | | | | | | |
|---|---|---|---|---|---|---|---|
| RSE 15/15 | NRF 40/20 | RFV 40/40 | RFN 40/20 | RSE 30/15 | RSE 15/30 | RSE 15/15 | RSE 20/20 |
| No's 1 | 1 | 4 | 1 | 1 | 8 | 7 | 1 |

TABLE 13

Barrel temperature profile (° C.) for Example 7

| B1 | B2 | B3 | B4 | B5 |
|---|---|---|---|---|
| 30 | 30 | 140 | 140 | 140 |

TABLE 14

Parameters for pre mix and granules of Example 7

| Parameters | Pre mix | Granules |
|---|---|---|
| Loss on drying (%) (75° C. for 5 minutes) | 0.15 | — |
| Retained Carbon dioxide content (%) | — | 95.71 |
| Bulk density (g/cc) | 0.981 | 0.646 |
| Tapped density (g/cc) | 1.193 | 0.873 |
| Compressibility index (%) | 17.72 | 26.09 |
| Hausner's ratio | 1.215 | 1.350 |
| Median diameter (microns) | 380 | 500 |

Note:
Retained Carbon dioxide content (%) of granules is reported in comparison to the pre mix.

TABLE 15

Quantitative compositions of Metformin for Examples 8-10

|  | Ex 8 Metformin HCL 500 mg | | Ex 9 Metformin HCL 500 mg + Sitagliptin 50 mg | | Ex 10 Metformin HCL 500 mg + Saxagliptin 5 mg | |
|---|---|---|---|---|---|---|
| Ingredients | % w/w | mg/tablet | % w/w | mg/tablet | % w/w | mg/tablet |
| Metformin HCL | 12.55 | 502.01 | 12.55 | 502.01 | 12.55 | 502.01 |
| Sitagliptin Phosphate | — | — | 1.56 | 62.53 | — | — |
| Saxagliptin HCL monohydrate | — | — | — | — | 0.15 | 6.14 |
| Placebo potassium bicarbonate granules | 84.79 | 3391.99 | 83.23 | 3329.46 | 84.65 | 3385.85 |
| Strawberry flavour | 0.05 | 2 | 0.05 | 2 | 0.05 | 2 |
| Acesulfame potassium | 0.6 | 24 | 0.6 | 24 | 0.6 | 24 |
| Sodium benzoate | 2 | 80 | 2 | 80 | 2 | 80 |
| Total | 100 | 4000 | 100 | 4000 | 100 | 4000 |

Example 8

Metformin Hydrochloride 500 mg Tablets

Manufacturing Process:

Placebo potassium bicarbonate effervescent granules (as per Example 7), were passed through #20 mesh sieve and mixed with Metformin hydrochloride, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Example 9

Metformin Hydrochloride 500 mg and Sitagliptin 50 mg Tablets

Manufacturing Process:

Placebo potassium bicarbonate effervescent granules (as per Example 7), were passed through #20 mesh sieve and mixed with Metformin hydrochloride, Sitagliptin phosphate, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Example 10

Metformin Hydrochloride 500 mg and Saxagliptin 5 mg Tablets

Manufacturing Process:

Placebo potassium bicarbonate effervescent granules (as per Example 7), were passed through #20 mesh sieve and mixed with Metformin hydrochloride, Saxagliptin hydrochloride monohydrate, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Example 11

Placebo Sodium Bicarbonate Effervescent Granules

TABLE 16

Quantitative composition of placebo sodium bicarbonate effervescent granules

| Ingredients | Ex 11 % w/w |
|---|---|
| Citric acid anhydrous | 44.55 |
| Sodium bicarbonate | 50.28 |
| Sodium carbonate | 5.16 |
| Total | 100 |

Manufacturing Process:

Citric acid anhydrous, sodium bicarbonate and sodium carbonate were deagglomerated and dried individually at 45° C. for 3 hours, and were blended and immediately processed in a co-rotating twin screw processor (Machine: Omega 20, L/D: 30) at a screw speed of 600 rpm and a feed rate of 300 g/min at processing area relative humidity of 20%±5% RH % and temperature of 30° C.±2° C.

TABLE 17

Screw configuration for Example 11

| Elements | | | | | | | |
|---|---|---|---|---|---|---|---|
| RSE 15/15 | NRF 40/20 | RFV 40/40 | RFN 40/20 | RSE 30/15 | RSE 15/30 | RSE 15/15 | RSE 20/20 |
| No's 1 | 1 | 4 | 1 | 1 | 8 | 7 | 1 |

TABLE 18

Barrel temperature profile (° C.) for Example 11

| B1 | B2 | B3 | B4 | B5 |
|---|---|---|---|---|
| 30 | 30 | 200 | 200 | 200 |

TABLE 19

Parameters for pre mix and granules of Example 11

| Parameters | Pre mix | Granules |
|---|---|---|
| Loss on drying (%) (75° C. for 5 minutes) | 0.15 | — |
| Retained Carbon dioxide content (%) | — | 97.90 |
| Bulk density (g/cc) | 0.976 | 0.698 |
| Tapped density (g/cc) | 1.460 | 0.953 |
| Compressibility index (%) | 33.33 | 26.76 |
| Hausner's ratio | 1.50 | 1.36 |
| Median diameter (microns) | 280 | 330 |

Note:
Retained Carbon dioxide content (%) of granules is reported in comparison to the pre mix

Example 12

Metformin Hydrochloride 500 mg Tablets

Manufacturing Process:

Placebo sodium bicarbonate effervescent granules (as per Example 11), were passed through #20 mesh sieve and mixed with Metformin hydrochloride, acesulfame potassium and strawberry flavor that were all passed through #60 mesh sieve and sodium benzoate (passed through #100 mesh sieve). This mixture was compressed using a rotary tablet compression machine (Machine: Riddi Pharma rotary press) using 25 mm round flat face beveled edge tooling.

Example 13

Metformin Hydrochloride 500 mg and Sitagliptin 50 mg Tablets

Manufacturing Process:

Placebo sodium bicarbonate effervescent granules (as per Example 11), were passed through #20 mesh sieve and mixed with Metformin Hydrochloride, Sitagliptin phosphate, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

TABLE 20

Quantitative compositions of Metformin for Examples 12-14

| | Ex 12 Metformin HCL 500 mg | | Ex 13 Metformin HCL 500 mg + Sitagliptin 50 mg | | Ex 14 Metformin HCL 500 mg + Saxagliptin 5 mg | |
|---|---|---|---|---|---|---|
| Ingredients | % w/w | mg/tablet | % w/w | mg/tablet | % w/w | mg/tablet |
| Metformin HCL | 12.55 | 502.01 | 12.55 | 502.01 | 12.55 | 502.01 |
| Sitagliptin Phosphate | | | 1.56 | 62.53 | | |
| Saxagliptin HCL monohydrate | | | | | 0.15 | 6.14 |
| Placebo sodium bicarbonate granules | 84.79 | 3391.99 | 83.24 | 3329.46 | 84.65 | 3385.85 |
| Strawberry flavour | 0.05 | 2 | 0.05 | 2 | 0.05 | 2 |
| Acesulfame potassium | 0.6 | 24 | 0.6 | 24 | 0.6 | 24 |
| Sodium benzoate | 2 | 80 | 2 | 80 | 2 | 80 |
| Total | 100 | 4000 | 100 | 4000 | 100 | 4000 |

Example 14

Metformin Hydrochloride 500 mg and Saxagliptin 5 mg Tablets

Manufacturing Process:
Placebo sodium bicarbonate effervescent granules (as per Example 11), were passed through #20 mesh sieve and mixed with Metformin Hydrochloride, Saxagliptin Hydrochloride monohydrate, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

TABLE 21

Quantitative compositions of Metformin for Examples 15-17

| Ingredients | Ex 15 Metformin HCL 500 mg | | Ex 16 Metformin HCL 500 mg + Sitagliptin 50 mg | | Ex 17 Metformin HCL 500 mg + Saxagliptin 5 mg | |
|---|---|---|---|---|---|---|
|  | % w/w | mg/tablet | % w/w | mg/tablet | % w/w | mg/tablet |
| Metformin HCL | 12.55 | 502.01 | 12.55 | 502.01 | 12.55 | 502.01 |
| Sitagliptin Phosphate | — | — | 1.56 | 62.53 |  |  |
| Saxagliptin HCL monohydrate | — | — | — | — | 0.15 | 6.14 |
| Placebo sodium bicarbonate granules | 42.4 | 1695.99 | 41.62 | 1664.73 | 42.32 | 1692.92 |
| Placebo potassium bicarbonate granules | 42.4 | 1695.99 | 41.62 | 1664.73 | 42.32 | 1692.92 |
| Strawberry flavour | 0.05 | 2 | 0.05 | 2 | 0.05 | 2 |
| Acesulfame potassium | 0.6 | 24 | 0.6 | 24 | 0.6 | 24 |
| Sodium benzoate | 2 | 80 | 2 | 80 | 2 | 80 |
| Total | 100 | 4000 | 100 | 4000 | 100 | 4000 |

Example 15

Metformin Hydrochloride 500 mg Tablets

Manufacturing Process:
Placebo sodium bicarbonate effervescent granules (as per Example 11) and placebo potassium bicarbonate effervescent granules (as per Example 7), were passed through #20 mesh sieve and mixed with Metformin Hydrochloride, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Example 16

Metformin Hydrochloride 500 mg and Sitagliptin 50 mg Tablets

Manufacturing Process:
Placebo sodium bicarbonate effervescent granules (as per Example 11) and placebo potassium bicarbonate effervescent granules (as per Example 7), were passed through #20 mesh sieve and mixed with Metformin Hydrochloride, Sitagliptin phosphate, acesulfame potassium and strawberry flavor that were all passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Example 17

Metformin Hydrochloride 500 mg and Saxagliptin 5 mg Tablets

Manufacturing Process:
Placebo sodium bicarbonate effervescent granules (as per Example 11) and placebo potassium bicarbonate effervescent granules (as per Example 7) were passed through #20 mesh sieve and mixed with Metformin Hydrochloride, Saxagliptin hydrochloride monohydrate, acesulfame potassium and strawberry flavor that were passed through #60 mesh sieve, and sodium benzoate (passed through #100 mesh sieve). This mixture was compressed using a rotary tablet compression machine (Machine: Riddi Pharma rotary press) using 25 mm round flat face beveled edge tooling.

Below are the tablet parameters of the examples mentioned herein.

TABLE 22

Tablet parameters for examples mentioned herein

| Tablet parameters | Ex 2 | Ex 3 | Ex 4 | Ex 6 | Ex 8 | Ex 9 | Ex 10 | Ex 12 | Ex 13 | Ex 14 | Ex 15 | Ex 16 | Ex 17 |
|---|---|---|---|---|---|---|---|---|---|---|---|---|---|
| Average Thickness (mm) (n = 5) | 5.69 | 5.86 | 5.82 | 5.88 | 5.21 | 5.22 | 5.19 | 5.33 | 5.36 | 5.43 | 5.34 | 5.34 | 5.33 |
| Average Hardness (kp) (n = 5) | 23.2 | 19.8 | 21.2 | 16.4 | 13.2 | 9.94 | 12.8 | 10.4 | 8.16 | 9.1 | 8.4 | 11.8 | 9.1 |

TABLE 22-continued

Tablet parameters for examples mentioned herein

| Tablet parameters | Ex 2 | Ex 3 | Ex 4 | Ex 6 | Ex 8 | Ex 9 | Ex 10 | Ex 12 | Ex 13 | Ex 14 | Ex 15 | Ex 16 | Ex 17 |
|---|---|---|---|---|---|---|---|---|---|---|---|---|---|
| Average Disintegration time (secs) (n = 3) | 42 | 75 | 43 | 54 | 33 | 51 | 47 | 53 | 51 | 57 | 45 | 54 | 38 |

TABLE 23

Quantitative compositions of Metformin for Examples 18-19

| | Ex 18 Metformin HCL 250 mg & Sitagliptin 50 mg | | Ex 19 Metformin HCL 1000 mg & Sitagliptin 50 mg | |
|---|---|---|---|---|
| Ingredients | % w/w | mg/tablet | % w/w | mg/tablet |
| Metformin HCL (Equivalent to 1000 mg Metformin HCL) | — | — | 25.10 | 1004.01 |
| Metformin HCL granules (Equivalent to 250 mg Metformin HCL) | 50.00 | 2000.00 | — | — |
| Sitagliptin Phosphate (Equivalent to 50 mg Sitagliptin) | 1.563 | 62.53 | 1.563 | 62.53 |
| Placebo sodium bicarbonate granules | — | — | 70.686 | 2827.45 |
| Strawberry flavour | 0.05 | 2.00 | 0.05 | 2.00 |
| Sucralose | 0.6 | 24 | 0.6 | 24.00 |
| Sodium benzoate | 2 | 80 | 2 | 80.00 |
| Total | 100 | 2168.53 | 100 | 4000.00 |

Example 18

Metformin Hydrochloride 250 mg & Sitagliptin 50 mg Tablets

Manufacturing Process:

Metformin hydrochloride effervescent granules (as per Example 1) were passed through #16 mesh sieve and mixed with sitagliptin phosphate, sucralose, strawberry flavor which were all passed through #60 mesh sieve, and sodium benzoate which was passed through #100 mesh sieve. This mixture was compressed using a rotary tablet compression machine (Machine: Riddi Pharma rotary press) using 20 mm round flat face beveled edge tooling.

Example 19

Metformin Hydrochloride 1000 mg & Sitagliptin 50 mg Tablets

Manufacturing Process:

Placebo sodium bicarbonate effervescent granules (as per Example 11), were passed through #20 mesh sieve and mixed with Metformin hydrochloride, Sitagliptin phosphate, sucralose, strawberry flavor which were all passed through #60 mesh sieve, and sodium benzoate which was passed through #100 mesh sieve. This mixture was compressed using a rotary tablet compression machine (Machine: Riddi Pharma rotary press) using 25 mm round flat face beveled edge tooling.

TABLE 24

Tablet parameters for examples 18 and 19

| Tablet parameters | Example 18 | Example 19 |
|---|---|---|
| Average Thickness (mm) (n = 5) | 4.458 | 5.954 |
| Average Hardness (kp) (n = 5) | 26.92 | 5.7 |
| Average Disintegration time (secs) (n = 3) | 85 | 78 |

The invention claimed is:

1. An effervescent metformin composition comprising:
   i. metformin,
   ii. an anhydrous acid component comprising a combination of a portion of the anhydrous acid component that has been melted and a remaining portion of the anhydrous acid component that has not been melted, wherein the portion of the anhydrous acid component that has been melted acts as an in-situ granulating agent;
   iii. an anhydrous base component comprising a carbonate functional group, wherein the base component is capable of reacting with the acid component to form carbon dioxide; and
   iv. optionally at least one other anti-diabetic agent;
   wherein the anhydrous acid component and the anhydrous base component are present in a weight ratio ranging from 3:1 to 1:5 and the composition does not include a binder or a granulating solvent other than the in-situ granulating agent;
   wherein the composition is in a form of granules; and
   wherein the composition has a retained carbon dioxide content of at least 90% of an input blend.

2. The effervescent metformin composition according to claim 1, wherein the composition further comprises one or more excipients and is compressed into a tablet.

3. The effervescent metformin composition according to claim 1, wherein the composition further comprises one or more excipients and is filled into a sachet.

4. A process for preparation of an effervescent metformin composition, comprising the steps of:
   (a) providing an input blend comprising an anhydrous acid component and an anhydrous base component, and processing the input blend through a twin-screw processor;
   (b) mixing a product of step (a) with metformin, and optionally at least one other anti-diabetic agent, and optionally at least one excipient;
   (c) compressing the mixed product into tablets or filling the mixed product into capsules or sachets following mixing in step (b),
   wherein a portion of the anhydrous acid component is melted in step (a) to serve as in-situ granulating agent, and wherein a remaining portion of the anhydrous acid component is not melted in step (a), and wherein the resulting effervescent metformin composition has a retained carbon dioxide content of at least 90% of the input blend.

5. A process for preparing an effervescent metformin composition, comprising the steps of:
   (a) providing an input blend comprising an anhydrous acid component, an anhydrous base component, and metformin, and processing the input blend through a twin-screw processor to form a product; and
   (b) compressing the product of step (a) into tablets or filling it into capsules or sachets after optionally mixing with at least one other anti-diabetic agent or at least one excipient,
   wherein a portion of the anhydrous acid component is melted in step (a) to serve as an in-situ granulating agent, and wherein a remaining portion of the anhydrous acid component is not melted in step (a), and
   wherein the resulting effervescent metformin composition has a retained carbon dioxide content of at least 90% of the input blend.

6. The process of claim 5, wherein step (a) additionally includes processing at least one other anti-diabetic agent through the twin-screw processor with the anhydrous acid component, the anhydrous base component, and metformin to form the product, and
   wherein step (b) includes compressing the product of step (a) into tablets or filling the product into capsules or sachets after optionally mixing with at least one excipient.

* * * * *